(12) United States Patent
Gelissen et al.

(10) Patent No.: US 12,303,242 B2
(45) Date of Patent: May 20, 2025

(54) OPTICAL VITAL SIGNS SENSOR

(71) Applicant: KONINKLIJKE PHILIPS N.V., Eindhoven (NL)

(72) Inventors: Jozef Hubertus Gelissen, Herten (NL); Rainer Hilbig, Aachen (DE); Achim Rudolf Hilgers, Alsdorf (DE); Mustafa Ghassan Radha, Steensel (NL); Koen Theo Johan De Groot, Sevenum (NL); Reinder Haakma, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 832 days.

(21) Appl. No.: 16/318,567

(22) PCT Filed: Jul. 24, 2017

(86) PCT No.: PCT/EP2017/068564
§ 371 (c)(1),
(2) Date: Jan. 17, 2019

(87) PCT Pub. No.: WO2018/019742
PCT Pub. Date: Feb. 1, 2018

(65) Prior Publication Data
US 2019/0282107 A1    Sep. 19, 2019

(30) Foreign Application Priority Data
Jul. 25, 2016 (EP) .................. 16181087

(51) Int. Cl.
*A61B 5/024* (2006.01)
*A61B 5/00* (2006.01)
*A61B 5/0225* (2006.01)

(52) U.S. Cl.
CPC ...... *A61B 5/02416* (2013.01); *A61B 5/02255* (2013.01); *A61B 5/6843* (2013.01); *A61B 5/681* (2013.01); *A61B 5/6824* (2013.01)

(58) Field of Classification Search
CPC ............ A61B 5/02416; A61B 5/02255; A61B 5/6843; A61B 5/681; A61B 5/6824
See application file for complete search history.

(56) References Cited

U.S. PATENT DOCUMENTS 5,485,838 A  1/1996  Ukawa et al.
2007/0055163 A1 * 3/2007  Asada .................. A61B 5/6838
                                                     600/490

(Continued)

FOREIGN PATENT DOCUMENTS

CN  104688202 A  6/2015
JP  2006239114 A  9/2006

(Continued)

OTHER PUBLICATIONS

Yilmaz, T. et al., "Detecting Vital Signs with Wearable Wireless Sensors", Sensors, 2010, London.

(Continued)

*Primary Examiner* — Alex M Valvis
*Assistant Examiner* — Justin Xu

(57) ABSTRACT

An optical vital signs sensor (100) is provided, which comprises a PPG sensor (102), a force transducer (130) configured to measure a force applied via the PPG sensor (102) to a skin (1000) of the user and a processing unit (140) configured to extract information regarding a blood volume pulse from the output of the PPG sensor (102) and to map the extracted information to the blood pressure value at a specific force applied to the PPG sensor (102).

20 Claims, 5 Drawing Sheets

(56) References Cited

U.S. PATENT DOCUMENTS

| | | |
|---|---|---|
| 2007/0167844 A1 | 7/2007 | Asada et al. |
| 2009/0124912 A1* | 5/2009 | McEwen ............ A61B 5/02255 |
| | | 600/495 |
| 2011/0208069 A1 | 8/2011 | Sawanoi et al. |
| 2012/0215118 A1 | 8/2012 | Chen et al. |
| 2015/0018637 A1 | 1/2015 | Chen et al. |
| 2016/0022220 A1 | 1/2016 | Lee |
| 2017/0188973 A1* | 7/2017 | Banet ................... A61B 5/7275 |
| 2018/0325398 A1* | 11/2018 | Nitzan ................. A61B 5/7278 |

FOREIGN PATENT DOCUMENTS

| | | |
|---|---|---|
| WO | 2011082341 A1 | 7/2011 |
| WO | 2014089665 A1 | 6/2014 |
| WO | 2016040263 A1 | 3/2016 |

OTHER PUBLICATIONS

"Vital signs monitoring market—Landscape analysis of blood pressure monitoring devices, pulse oximeters and temperature monitoring devices", Markets and Markets, Forecast up to 2018, 2013.

McGhee, B et al., "Monitoring Arterial Blood Pressure: What You May Not Know", Critical Care Nurse, 2002.

Alpert, B. et al., "Oscillometric blood pressure: a review for clinicians", Journal of the American Society of Hypertension, 2014.

Monte-Moreno, E., "Non-invasive estimate of blood glucose and blood pressure from a photoplethysmograph by means of machine learning techniques", Artificial Intelligence in Medicine, 2011.

Elgendi, M., "On the Analysis of Fingertip Photoplethysmogram Signals", Current Cardiology Reviews, 2012.

* cited by examiner

OPTICAL VITAL SIGNS SENSOR

CROSS-REFERENCE TO PRIOR APPLICATIONS

This application is the U.S. National Phase application under 35 U.S.C. § 371 of International Application No. PCT/EP2017/068564, filed on 24 Jul. 2017, which claims the benefit of European Patent Application No. 16181087.4, filed on 25 Jul. 2016. These applications are hereby incorporated by reference herein.

FIELD OF THE INVENTION

The invention relates to an optical vital signs sensor for monitoring vital signs of a user.

BACKGROUND OF THE INVENTION

Heart rate sensors like optical heart rate sensors are well known to monitor or detect vital signs like a heart rate of a user. Such a heart rate sensor can be based on a photoplethysmograph (PPG) sensor and can be used to acquire a volumetric organ measurement. By means of pulse oximeters, changes in light absorption of a human skin are detected and based on these measurements a heart rate or other vital signs of a user can be determined. The PPG sensors comprise a light source like a light emitting diode (LED) which is emitting light into the skin of a user. The emitted light is scattered in the skin and is at least partially absorbed by the blood. Part of the light exits the skin and can be captured by a photo detector. The amount of light that is captured by the photo detector can be an indication of the blood volume inside the skin of a user. A PPG sensor can thus monitor the perfusion of blood in the dermis and subcutaneous tissue of the skin through an absorption measurement at a specific wave length. If the blood volume is changed due to the pulsating heart, the scattered light coming back from the skin of the user is also changing. Therefore, by monitoring the detected light signal by means of the photo detector, a pulse of a user in his skin and thus the heart rate can be determined. Furthermore, compounds of the blood like oxygenated or de-oxygenated hemoglobin as well as oxygen saturation can be determined.

The PPG sensor can be implemented for example in a smart watch and can be placed in direct contact with the skin of the user. If the PPG sensor is, however, not anymore in direct contact with the skin of the user, e.g. if a loss of skin contact has occurred, the output of the photo detector cannot be used to detect vital signs of a user.

Vital signs of a user can be the heart rate, the respiration rate, the core temperature and the blood pressure of the user.

WO 2016/040263 A1 discloses a wrist worn device for determining a pressure of blood of a user. An accelerometer is provided to detect when a blood pressure pulse is propagated. A PPG sensor or a pulse pressure sensor detects the arrival of the blood pressure at the user's wrist. The output signal of the accelerometer and the PPG sensor are processed to calculate a pulse transit time and to generate a pulse pressure value based on the pulse transient time.

US 2007/0167844 A1 discloses an optical vital signs sensor with a PPG sensor which is used to determine a blood pressure.

WO 2011/082341 A1 discloses an optical vital signs sensor with a PPG sensor, wherein the output of the PPG sensor is used to determine a blood pressure.

US 2012/0215118 A1 discloses a cuff for determining a blood pressure of the user. The cuff also comprises a PPG sensor.

US 2011/0208069 A1 discloses a blood pressure information measuring device which includes a PPG sensor.

US 2007/0055163 A1 discloses a wearable blood pressure sensor which also comprises a PPG sensor.

JP 2006/239114 A1 discloses a blood pressure monitor having a PPG sensor.

SUMMARY OF THE INVENTION

It is an object of the invention to provide an optical vital signs sensor which allows an improved detection or estimation of vital signs of a user.

According to an aspect of the invention a (wrist worn) optical vital signs sensor is provided to measure or determine vital signs of a user. The optical vital signs sensor is a photoplethysmographic sensor (PPG). A light source is configured to generate light which is directed towards a skin of the user. The sensor also comprises a photo detector unit configured to detect light which is indicative of a reflection of light emitted in or from the skin of the user. The PPC sensor comprises a contact surface configured to be placed against a skin of a user. The light from the light source is directed towards the skin of the user via the contact surface. The optical vital signs sensor further comprises a force transducer or force measuring unit to measure a force applied via the PPG sensor to the skin of the user. Furthermore, the sensor comprises a processing unit to extract information regarding a blood volume pulse from an output signal of the PPG sensor and to map the extracted information to a blood pressure value at a specific force applied to the PPG sensor. With such a (wrist worn) optical vital signs sensor, it is thus possible to estimate the blood pressure of a user in a non-invasive matter. Furthermore, the blood pressure of the user can be estimated at any time by means of the (wrist worn) optical vital signs sensor.

According to an aspect of the invention, the force at which the PPG sensor is pressed against the skin of the user is induced by the user himself.

According to a further aspect of the invention, the wrist worn optical vital signs sensor comprises a force actuator to apply a force to the skin of the user via the PPG sensor in order to start the measuring process to estimate the blood pressure of a user.

According to a further aspect of the invention, the wrist worn optical vital signs sensor comprises a wrist band with a cavity in which a distensible membrane is arranged. The membrane can be inflated or deflated by means of an air pump unit in order to apply a force to the PPG sensor to press the PPG sensor against the skin of the user. According to a further aspect of the invention, the force transducer is coupled to the PPG sensor in order to detect a force at which the PPG sensor is pressed against a skin of the user.

According to a further aspect of the invention, the force applied to the skin of a user is >15 N.

The invention also relates to a method of measuring or determining vital signs of a user with a wrist worn optical vital signs sensor. The optical vital signs sensor is a PPG sensor having a contact surface, at least one light source for generating light which is directed towards the skin of the user and at least one photo detector to detect light which is indicative of a reflection of light emitted in or from the skin of the user. A force is applied to the PPG sensor when the PPG sensor is pressed against a skin of the user. Light from the at least one light source is emitted towards the skin of the user and the reflective light is detected. The force at which the PPG sensor is pressed against the skin of the user is measured. Blood volume pulse information is extracted from an output signal of the PPG sensor and the extracted blood volume pulse information is mapped to a blood pressure value at a specific force applied to the PPG sensor.

According to an aspect of the invention, a blood pressure is measured with an external device like a typical blood pressure cuff and the mapping of the blood volume pulse information to a blood pressure value is calibrated based on the blood pressure as measured by the external device. This is advantageous as it allows a calibration of the determination of the blood pressure with a blood pressure measured from an external device. With such a calibration step, the accuracy of the determination of the blood pressure should be significantly increased.

The force transducer or the force measuring unit can detect or measure the force directly e.g. by means of a force sensor. Alternatively, the force can be determined indirectly.

According to an aspect of the invention, the blood pressure value corresponds to the Mean Arterial Pressure MAP.

According to an aspect of the invention, the force applied to the skin of the user is only applied by the PPG sensor and its contact surface.

According to an aspect of the invention, a computer program product comprising a computer readable memory storing computer program code means for causing the optical vital signs to carry out the steps of measuring or determining vital signs of a user as described above is provided.

According to an aspect of the invention, the vital signs sensor comprises a LED based PPG sensor. The LED light penetrates the skin of the user, is reflected and some of it can reach a photo detector. The output of the photo detector can be used to monitor a blood volume fraction and blood compounds like oxygenated and de-oxygenated hemoglobin. In particular, the amount of absorption or reflectance of the light from the LED light source can be used to determine the heart rate as well as the blood volume fraction or blood compounds. The heart rate relates to the blood volume fraction. Furthermore, the PPG sensor according to the invention is therefore an optical sensor allowing a non-invasive measurement of vital signs of a user.

It shall be understood that a preferred embodiment of the present invention can also be a combination of the dependent claims or above embodiments or aspects with respective independent claims.

These and other aspects of the invention will be apparent from and elucidated with reference to the embodiment(s) described hereinafter.

DETAILED DESCRIPTION OF EMBODIMENTS

Figure 1:
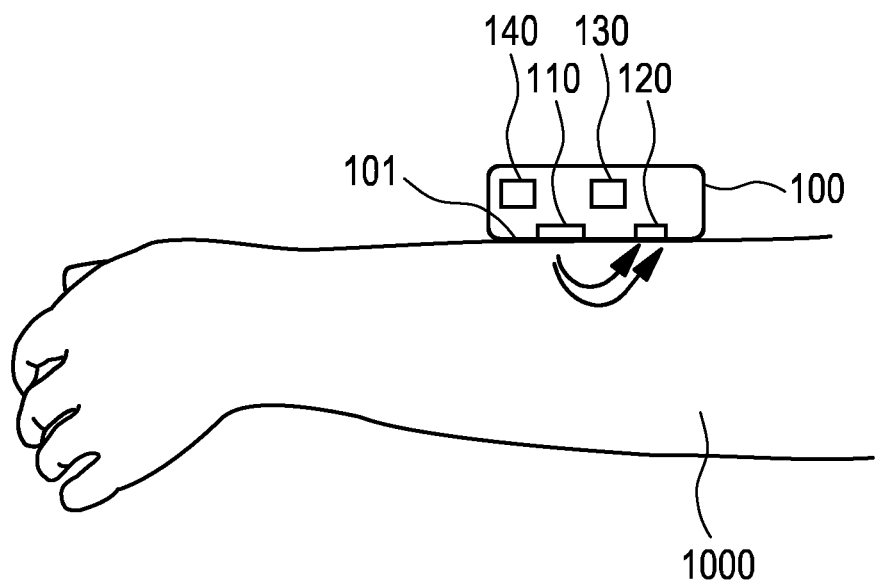
FIG. 1 shows a schematic representation of a vital signs sensor according to the invention.

FIG. 1 shows a basic representation of an operational principle of an optical vital signs sensor. In FIG. 1, the optical vital signs sensor, e.g. a heart rate sensor 100, with its contact surface 101 is arranged or placed on for example an arm of a user. The contact surface 101 can be (directly) placed onto the skin 1000 of the user. The heart rate sensor 100 comprises at least one light source 110 and at least one photo detector 120. The light source 110 emits light via the contact surface 101 onto or in the skin 1000 of a user. Some of the light is reflected and the reflected light can be detected by the photo detector 120. Some light can be transmitted through tissue of the user and be detected by the photo detector 120. Based on the reflected light, vital signs of a user like a heart rate can be determined.

According to the invention, pressure is applied to small vessels within the skin organ (skin arterioles).

The optical vital signs sensor 100 furthermore comprises a force transducer 130 which is able to measure the force applied to the skin 1000 of the user via the contact surface 101. In other words, the force transducer 130 can measure the force with which the sensor is pressed against the skin of the user. The optical vital signs sensor 100 furthermore comprises a processing unit 140 which is used to estimate a blood pressure of a user.

The vital signs sensor 100 can be implemented as a PPG sensor or may comprise a PPG sensor. The output signal of the PPG sensor gives an indication on the blood movement in vessels of a user. The quality of the output signal of the PPG sensor can depend on the blood flow rate, skin morphology and skin temperature. In addition, optical losses in the PPG sensor may also have an influence on the quality of the output signal of the PPG sensor. The optical efficiency of the PPG sensor can depend on reflection losses when light penetrates from one media into another. Furthermore, scattering of light at the surface of the skin of the user may also have an influence on the optical efficiency of the PPG sensor.

The PPG sensor or optical vital signs sensor according to an aspect of the invention can be implemented as a device that requires a contact with the skin of the user such as a wrist worn device (like a watch or smart watch).

Figure 2:
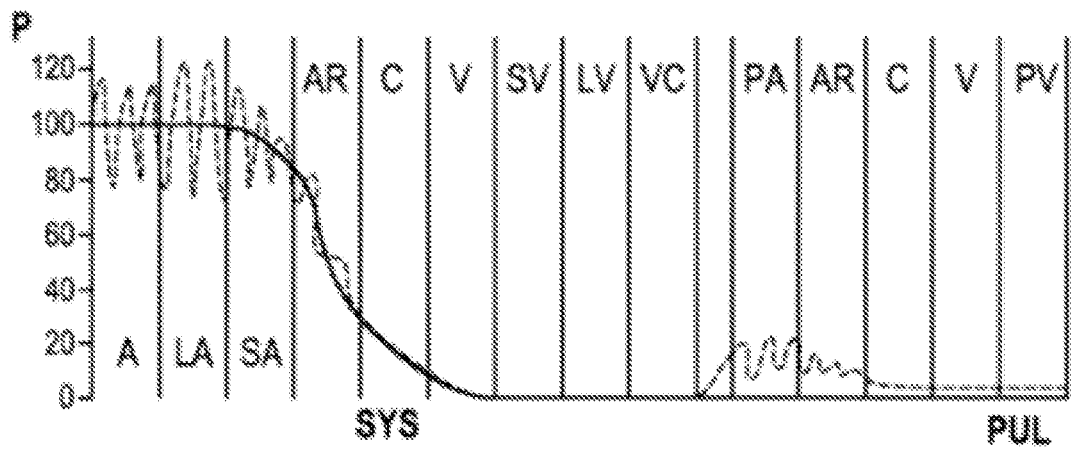
FIG. 2 shows a graph indicating blood pressure in several vessels of a user.

FIG. 2 shows a graph indicating blood pressure P in several vessels of a user. The graph thus depicts the pressure P (mmHg) in the systematic SYS and the pulmonary PUL phase.

These vessels include the aorta A, large arteries LA, small arteries SA, arterioles AR, capillaries C, venules V, small veins SV, large veins LV, vena cava VC and pulmonary veins PV. As can be seen from FIG. 2, the pressure within the arterioles for example is also regulated or influenced by the pressure in the larger arteries. However, the value of the pressure is much lower.

According to the invention, a (wrist worn) optical vital signs sensor having a PPG sensor together with a force applied to the skin of a user is used in a non-invasive way to measure or estimate the blood pressure of a user. In order to estimate the blood pressure of a user, a force is applied to the skin 1000 of the user via a contact surface 101 of the sensor 100. The output of the photo detector 120 is measured and based on these measurements together with an estimation of the applied force, the blood pressure is estimated by the processing unit 140.

According to the invention, the PPG sensor is used to detect variations in the blood volume pulse when no pressure is applied to the skin of the user as well as when pressure is applied to the skin of the user. In particular, according to the invention, blood pressure estimation is performed by analyzing the reaction of the blood volume pulse in the skin arterioles in response to an external force applied locally to the skin of a user.

According to an aspect of the invention, the force applied to the PPG sensor is first increased (ramp up) and then decreased (ramp down). According to the invention, the output signal of the PPG sensor during the ramping up of the force applied to the PPG sensor is used to determine the blood pressure of a user.

Figure 3:
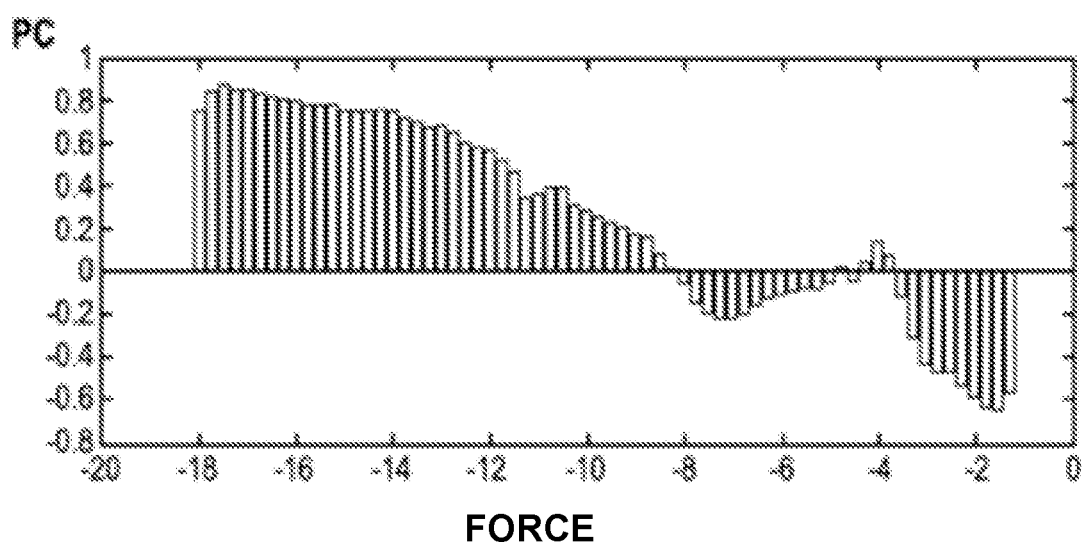
FIG. 3 shows a graph indicating a correlation between a pulsatile AC component of the output of the photo detector and a mean arterial pressure as a function of an applied force.

FIG. 3 shows a graph indicating a correlation between a strength of the pulsatile AC component PC of the output of the photo detector and a mean arterial pressure MAP as a function of the force applied to the sensor. In particular, the relation between the strength of the AC component of the output signal of the photo detector and the mean arterial pressure under different force levels applied to the vital signs sensor are depicted. A "negative" applied force relates to a higher level of pressure on the skin. As can be seen from FIG. 3, the strength of the AC component of the output signal of the photo detector highly correlates with the mean arterial pressure MAP starting with force levels at 15 N or stronger. As can be seen from FIG. 3, the best result is obtained at a force of 17.25 N with a correlation of r=0.87.

Figure 4:
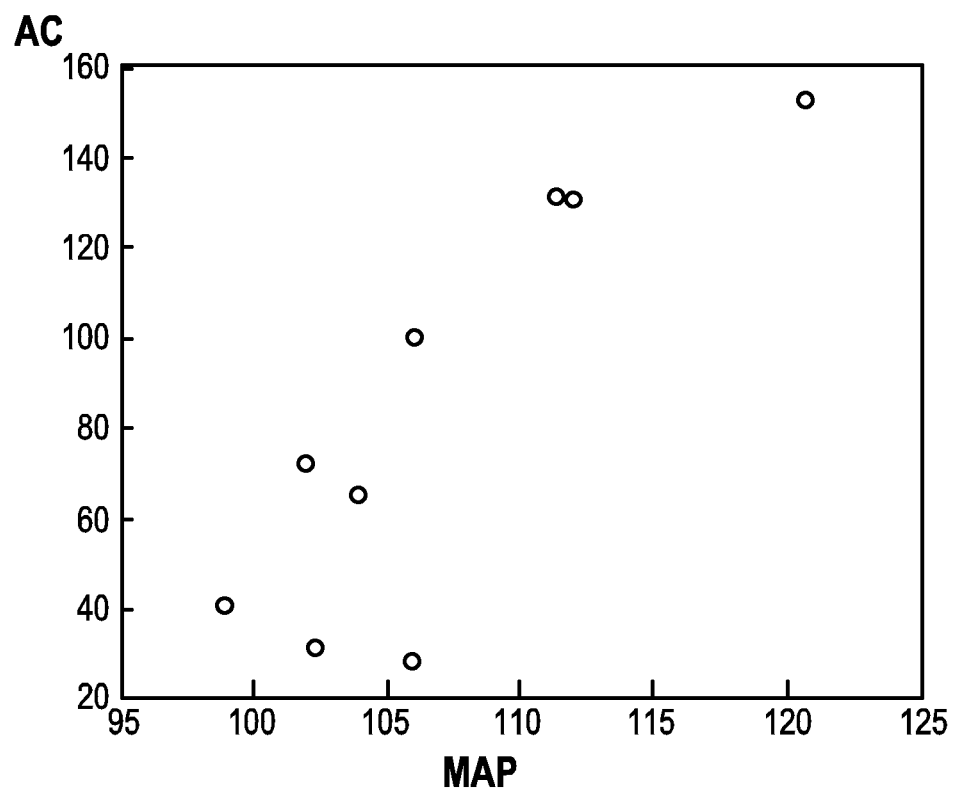
FIG. 4 shows a scatter plot between the mean arterial pressure and the AC component of the output signal of the photo detector.

FIG. 4 shows a scatter plot between the mean arterial pressure and the AC component AC of the output signal of the photo detector. FIG. 4 therefore shows a correlation diagram between the mean arterial pressure and the value of the AC component of the photo detector at an applied force of 17.25 N.

Figure 5:
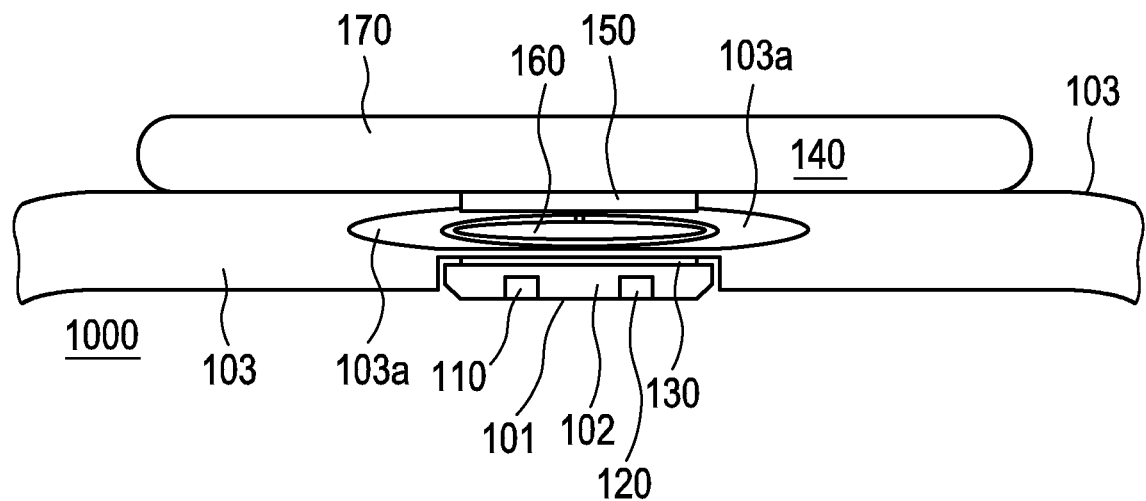
FIG. 5 shows a schematic cross section of an optical vital signs sensor according to a first embodiment of the invention.

FIG. 5 shows a schematic cross section of an optical vital signs sensor according to a first embodiment of the invention. The vital signs sensor 100 according to the first embodiment can be implemented as a wrist worn device like a smart watch. The device 100 comprises a wrist band 103, a PPG sensor 102, a force transducer 130, a processing unit 140 optionally, an air pump unit 150, optionally a distensible membrane 160 and optionally a display 170. In the wrist band 103 a cavity 103*a* can be present. The distensible membrane 160 can be arranged inside the cavity 103*a*. The distensible membrane 160 can be arranged over the PPG sensor 102. Between the PPG sensor 102 and the membrane 160, the force transducer 130 is arranged.

According to the invention, the device is provided with a force actuator or compression unit. The compression unit 150, 160 is implemented by the air pump unit 150 and the distensible membrane 160. The compression unit 150, 160 is used to exert force on the PPG sensor 102 such that the PPG sensor 102 is pressed against the skin of a user. The PPG sensor 102 comprises at least one light emitting diode 110 and at least one photo diode 120. The function of the PPG sensor 102 corresponds to the function of the PPG sensor according to FIG. 1. The PPG sensor 102 is used as a blood volume sensor and measures volumetric changes of the blood flow in the skin arterioles. The force transducer 130 (arranged between the PPG sensor 102 and the compression unit 160, 150) is used to measure the locally applied force on the PPG sensor 102. The processing unit 140 receives the output of the PPG sensor 102 and extracts features from the PPG sensor to estimate a blood pressure. Optionally, the result of the blood pressure estimation can be displayed on the display 170.

The wristband 103 can be implemented as a flexible strap having two ends with a securement means to circumferentially fasten the strap around a waist of a user. By means of the compression means 150, 160, the PPG sensor 102 is pressed against the skin 1000 of the user. The PPG sensor 102 is used to detect blood volume changes in particular in the skin arterioles 1001. The compression means 150, 160 comprises a distensible membrane 160 which can be embedded as a distensible air bag which can be inflated or deflated by means of the air pump unit 150.

Alternatively, a force can be applied to the PPG sensor 102 by reducing or shrinking the inner circumference of the wristband 103 thus pressing the PPG sensor 102 against the skin of a user.

The force transducer 130 is used to detect the external force being applied to the PPG sensor 102 pressing the PPG sensor 102 against the skin of the user. The force transducer 130 can be implemented as a strain gauge or a piezo electric sensor. According to an aspect of the invention, the detected force can be converted into an electronic signal and can be forwarded to the processor 140.

The PPG sensor 102 can have green LEDs 110. The light from the LEDs is directed into the skin surface and the photo diode 120 is used to detect the amount of reflected light. During each cardiac cycle, the amount of reflected light varies due to the varying amount of blood flowing through the arterioles. A variation in the skin-tone over time may contain information on the blood volume. The output signal of the PPG sensor can be forwarded to the processing unit 140.

Preferably, the user should keep his wrist and the wrist worn device at the level of his heart during the measurement period. The blood pressure estimation procedure may be initiated by the user for example by pressing a button. According to the first embodiment, the compression unit 150, 160 is activated in order to apply pressure on the PPG sensor 102 thereby pressing the PPG sensor into the skin of the user. The PPG sensor 102 will then detect blood volume variations of the blood in the skin arterioles. The force applied to the skin of the user can linearly increase from 0 N to a predefined maximum value.

The output of the PPG sensor 102 as well as the output of the force transducer 130 are forwarded to the processing unit 140. The processing unit 140 may comprise a unit for assessing the quality of the output of the sensor. The processing unit 140 may furthermore comprise an extraction unit for deriving real time features from the PPG output signal. These features may include the pulsatile AC component. Also other features describing the morphology of the PPG output signal may apply. The processing unit may also comprise a unit for selecting of which specific external force the extracted feature can be mapped to a blood pressure value by analyzing the sensor signal and its quality.

According to an aspect of the invention, the extracted PPG features may be combined with other physiologic or subject specific properties measured by the optical vital signs sensor. Alternatively, these features can be stored in a memory of the device. The relationship between the external force, features extracted from the PPG sensor output signal and blood pressure may be learned in an offline training stage. The calibration function which maps external force and features extracted from the PPG signal to a blood pressure estimate may also include parameters related to physiological or subject specific properties. Based on the detected features in the output signal of the PPG sensor 102 and the force as detected by the force transducer 130, the processing unit 140 estimates a blood pressure value. Optionally, this estimated blood pressure value can be displayed on the display 170. The pressure inside the membrane 160 can then be reduced.

Figure 6:
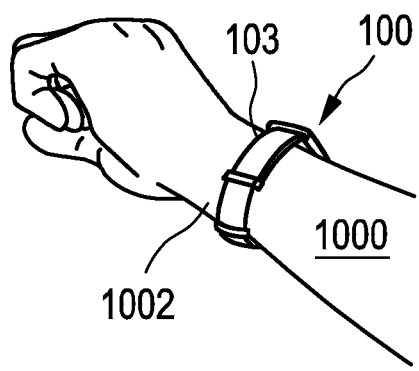
FIG. 6 shows a schematic representation of the optical vital signs sensor with a wrist band worn at the wrist of the user.

FIG. 6 shows a schematic representation of the optical vital signs sensor 100 with a wrist band 103 worn at a wrist 1002 of the user 1000.

Figure 7:
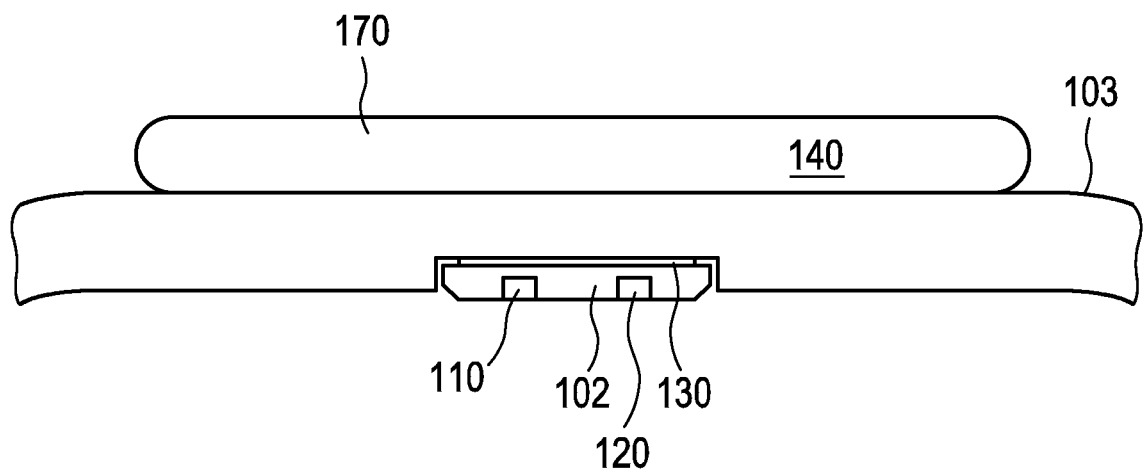
FIG. 7 shows a schematic cross section of an optical vital signs sensor according to a second embodiment.

FIG. 7 shows a schematic cross section of an optical vital signs sensor according to a second embodiment. The second embodiment of the optical vital signs sensor substantially corresponds to the optical vital signs sensor according to a first embodiment however without a dedicated compression means 150, 160. Thus, the optical vital signs sensor 100 according to a second embodiment comprises a wrist band 103, a PPG sensor 102, a force transducer 130 coupled to the PPG sensor 102 and optionally a display 170. The optical vital signs sensor furthermore comprises a processing unit 140.

According to the second embodiment, the user must apply the force to press the PPG sensor 100 against the skin of the user himself.

Figure 8:
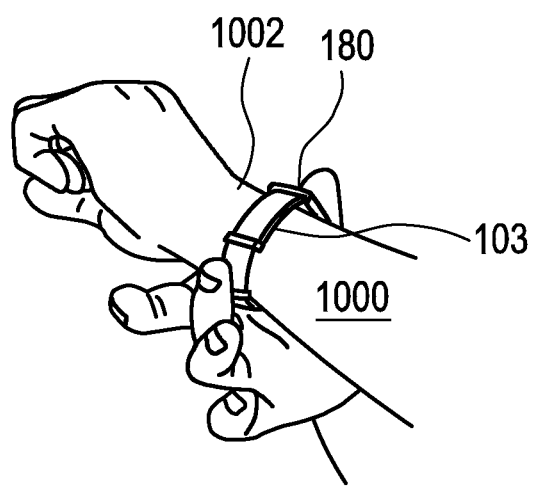
FIG. 8 shows a schematic representation of the optical vital signs sensor worn at the wrist of the user.

FIG. 8 shows a schematic representation of a wrist 1002 of a user together with the optical vital signs sensor during a measurement according to the second embodiment. Here, the user must apply the required force to press the PPG sensor 102 against the skin 1000 by pressing the optical vital signs sensor against his skin. The amount of pressure applied is detected by the force transducer 130. When the PPG sensor 102 is pressed against the skin of the user, the PPG sensor 102 can be activated to detect the variations in the blood volume in the skin arterioles. Optionally, the user may be guided by information on the display 170 through the measurement procedure. Once the processing unit has estimated the blood pressure (for example as described according to the first embodiment), the estimated blood pressure can be outputted via the display.

The second embodiment is in particular advantageous as a standard optical vital signs sensor having a PPG sensor only needs to be adapted by introducing a force transducer in order to be able to estimate the blood pressure according to the invention.

A third embodiment of the invention may be based on a combination of the first and second embodiment. According to the third embodiment, the user must compress the device in order to supply the required force to press the PPG sensor against the skin of the user. According to the third embodiment, the force transducer 130 measures the force with which the PPG sensor is pressed against the skin of the user. In order to reduce this force, the compression means can be controlled and deflected in order to reduce the force.

According to an aspect of the invention, an external device like a blood pressure cuff can be used to measure the blood pressure of the user, in particular when the PPG sensor is also determining the blood pressure of the user. The blood pressure of the external device can then be forwarded e. g. wirelessly or can be input into the PPG sensor. The processing unit 140 can then use this blood pressure value to calibrate the mapping of the blood pressure value or the determination of the blood pressure for this specific user. This calibration step can be performed on a daily, weekly or monthly basis. With such a calibration step, the accuracy of the determined blood pressure by the PPG sensor or by the processing unit 140 can be significantly increased.

The results of calibration (including the measured blood pressure of the cuff and/or the blood pressure determined by the PPG sensor) can be forwarded to a server for further analysis to improve the algorithm in the PPG sensor.

Other variations of the disclosed embodiment can be understood and effected by those skilled in the art in practicing the claimed invention from a study of the drawings, the disclosure and the appended claims.

In the claims, the word "comprising" does not exclude other elements or steps and in the indefinite article "a" or "an" does not exclude a plurality.

A single unit or device may fulfil the functions of several items recited in the claims. The mere fact that certain measures are recited in mutual different dependent claims does not indicate that a combination of these measurements cannot be used to advantage. A computer program may be stored/distributed on a suitable medium such as an optical storage medium or a solid state medium, supplied together with or as a part of other hardware, but may also be distributed in other forms such as via the internet or other wired or wireless telecommunication systems.

Any reference signs in the claims should not be construed as limiting the scope.

The invention claimed is:

1. An optical vital signs sensor configured to measure or determine vital signs of a user, comprising:
   a photoplethysmographic (PPG) sensor comprising:
      a light source configured to generate light that is directed towards a skin of the user,
      a photo detector unit configured to detect light, wherein the light is indicative of a reflection of light emitted in or from the skin of the user, and
      a contact surface configured to be placed against a skin of a user,
      wherein an output of the PPG sensor comprises a DC component and an AC component,
   wherein the light from the light source is directed towards the skin of the user via the contact surface,
   a force measuring unit configured to measure a force applied via the contact surface of the PPG sensor to the skin of the user, and
   a processing unit configured to:
      extract information regarding a blood volume pulse from the AC component of the output signal of the PPG sensor during application of the force applied to the skin of the user,
      monitor the measured force, and, when the measured force reaches a predetermined force value, map the extracted information to a blood pressure value at the measured force, and
      communicate the blood pressure value to the user.

2. The optical vital signs sensor of claim 1, wherein the optical vital signs sensor is a wrist worn optical vital signs sensor.

3. The optical vital signs sensor of claim 2, wherein the force actuator is configured to apply a force to the skin of the user via the PPG sensor.

4. The optical vital signs sensor of claim 1, further comprising a wristband having a cavity in which a distensible membrane is arranged, wherein the membrane can be inflated or deflated by an air pump unit in order to apply pressure to the PPG sensor.

5. The optical vital signs sensor of claim 1, wherein the predetermined force value is at least 15 N.

6. The optical vital signs sensor of claim 1, wherein the blood pressure value is a Mean Arterial Pressure.

7. The optical vital signs sensor of claim 1, comprising a force actuator configured to apply the force to the skin of the user.

8. The optical vital signs sensor of claim 7, wherein the force transducer is coupled to the PPG sensor in order to detect the force at which the PPG sensor is pressed against a skin of a user.

9. The optical vital signs sensor of claim 1, comprising a display device that displays the blood pressure value.

10. A method of measuring or determining vital signs of a user with an optical vital signs sensor configured to measure or determine vital signs of a user, the optical vital signs sensor being a PPG sensor having a contact surface, wherein at least one light source generates light that is directed towards a skin of a user, and wherein at least one photo detector unit is configured to detect light that is indicative of a reflection of light emitted in or from the skin of a user, wherein an output of the PPG sensor comprises a DC component and an AC component, the method comprising:

applying the contact surface of the PPG sensor to the skin of a user, emitting light from at least one light source towards the skin of the user and detecting the reflective light by the at least one photo detector, measuring, by a force transducer, a measured force at which the contact surface of the PPG sensor is pressed against a skin of a user, extracting blood volume pulse information from the AC component of the output signal of the PPG sensor, monitoring the measured force, and, when the measured force reaches a predetermined force value, mapping the extracted blood volume pulse information to a blood pressure value at the measured force, and communicating the blood pressure value to the user.

11. The method of measuring or determining vital signs of a user of claim 10, further comprising:

measuring a blood pressure with an external device, and calibrating the mapping based on the measured blood pressure.

12. The method of measuring or determining vital signs of a user of claim 10, wherein only the contact surface of the PPG sensor is used to apply the force to the skin of the user.

13. The method of measuring or determining vital signs of a user of claim 10, wherein a force actuator applies a force that urges the contact surface of the PPG sensor to the skin of the user.

14. The method of claim 10, wherein communicating the blood pressure value to the user is via a display device.

15. A non-transitory computer-readable medium that includes a program that, when executed by a processor, causes the processor to:

receive a photoplethysmographic (PPG) signal from a PPG sensor that is in contact with skin of a user and detects a reflection of light emitted in or from the skin of the user, wherein the PPG signal comprises a DC component and an AC component, receive a force signal from a force transducer that measures a force applied by a surface of the PPG sensor to the skin of the user, extract pulsatile information regarding a blood volume pulse from the AC component of the PPG signal, monitor the measured force, and, when the measured force reaches a predetermined force value, determine a blood pressure value based on the pulsatile information and the measured force, and communicate the blood pressure value to the user.

16. The non-transitory computer-readable medium of claim 15, wherein the program causes the processor to control a force actuator to apply the force to the skin of the user.

17. The non-transitory computer-readable medium of claim 16, wherein the program causes the processor to:

control the force actuator to apply a linearly increasing force to the skin of the user, extract a plurality of pulsatile information from the AC component of the PPG signal and a corresponding plurality of measured force, wherein determining the blood pressure value is based on the plurality of pulsatile information and corresponding plurality of measured force.

18. The non-transitory computer-readable medium of claim 16, wherein the medium is included in a wrist-worn device that includes the PPG sensor, the force transducer, and the force actuator.

19. The non-transitory computer-readable medium of claim 15, wherein the medium is included in a wrist-worn device that includes the PPG sensor and the force transducer.

20. The non-transitory computer-readable medium of claim 15, wherein the processing unit communicates the blood pressure value to the user via a display device.

* * * * *